(12) United States Patent
Cohen et al.

(10) Patent No.: US 9,770,256 B2
(45) Date of Patent: Sep. 26, 2017

(54) APPARATUSES AND METHODS FOR CUTTING A TISSUE BRIDGE AND/OR REMOVING A HEART VALVE CLIP OR SUTURE

(71) Applicant: MITRACORE TECHNOLOGIES INC., Montreal (CA)

(72) Inventors: Gideon Cohen, Toronto (CA); Etienne Lagace, Montreal (CA); Marwane Berrada, Laval (CA); Charles Perkins, Montreal (CA); Boby Chu, Anjou (CA)

(73) Assignee: MITRACORE TECHNOLOGIES INC., Montreal, QC (CA)

( * ) Notice: Subject to any disclaimer, the term of this patent is extended or adjusted under 35 U.S.C. 154(b) by 482 days.

(21) Appl. No.: 14/348,527

(22) PCT Filed: Sep. 28, 2012

(86) PCT No.: PCT/US2012/058139
§ 371 (c)(1),
(2) Date: Mar. 28, 2014

(87) PCT Pub. No.: WO2013/049734
PCT Pub. Date: Apr. 4, 2013

(65) Prior Publication Data
US 2014/0228871 A1    Aug. 14, 2014

Related U.S. Application Data

(60) Provisional application No. 61/707,856, filed on Sep. 28, 2012, provisional application No. 61/540,156, filed on Sep. 28, 2011.

(51) Int. Cl.
*A61B 17/00* (2006.01)
*A61B 17/32* (2006.01)
(Continued)

(52) U.S. Cl.
CPC .... *A61B 17/320016* (2013.01); *A61B 17/295* (2013.01); *A61B 17/3201* (2013.01);
(Continued)

(58) Field of Classification Search
CPC .............. A61B 17/295; A61B 17/3201; A61B 17/320016; A61B 17/32053;
(Continued)

(56) References Cited

U.S. PATENT DOCUMENTS 4,312,337 A * 1/1982 Donohue ........... A61B 17/1796
606/103
5,071,428 A * 12/1991 Chin .................... A61N 1/0587
606/184

(Continued)

FOREIGN PATENT DOCUMENTS

DE     91 00 873 U1   4/1991
FR     2 705 556 A1   12/1994
(Continued)

OTHER PUBLICATIONS

Rose, David et al. "Late MitraClipFailure: Removal Technique for Leaflet-Sparing Mitral Valve Repair". Journal of Cardiac Surgery. Jul. 4, 2012 (Jul. 4, 2012).

(Continued)

*Primary Examiner* — Todd J Scherbel
*Assistant Examiner* — Son Dang

(57) ABSTRACT

A medical device for safely and effectively removing a clip or a suture from a heart valve is operable in association with a guidewire for positioning the device in proximity to the heart valve. The apparatus may include a blade for cutting a tissue bridge including the clip and an arrangement for removing the tissue bridge from the heart valve. The apparatus may include two arms that secure the clip. The blade may be deployed to core out a central portion of a tissue (Continued)

bridge, including the clip or the suture, from the heart valve. The blade may be activated by an actuator. A retrieval member may be configured to capture the tissue bridge and the clip or suture after excision by the blade.

4 Claims, 13 Drawing Sheets

(51) Int. Cl.
*A61B 17/295* (2006.01)
*A61B 17/3201* (2006.01)
*A61B 17/3205* (2006.01)
*A61B 17/29* (2006.01)
*A61B 10/06* (2006.01)
*A61B 17/22* (2006.01)
*A61B 17/30* (2006.01)
*A61B 17/34* (2006.01)

(52) U.S. Cl.
CPC ........ *A61B 17/32053* (2013.01); *A61B 10/06* (2013.01); *A61B 2017/00243* (2013.01); *A61B 2017/00323* (2013.01); *A61B 2017/00353* (2013.01); *A61B 2017/00398* (2013.01); *A61B 2017/00539* (2013.01); *A61B 2017/00623* (2013.01); *A61B 2017/22039* (2013.01); *A61B 2017/2905* (2013.01); *A61B 2017/2926* (2013.01); *A61B 2017/308* (2013.01); *A61B 2017/3488* (2013.01)

(58) Field of Classification Search
CPC A61B 2017/00243; A61B 2017/00353; A61B 2017/2905; A61B 2017/00398; A61B 2017/22039; A61B 2017/308; A61B 2017/00323; A61B 2017/00623; A61B 10/06; A61B 2017/00539; A61B 2017/2926; A61B 2017/3488

See application file for complete search history.

(56) References Cited

U.S. PATENT DOCUMENTS

| 5,820,630 A | * | 10/1998 | Lind | A61B 10/06 606/205 |
| 5,908,420 A | * | 6/1999 | Parins | A61B 18/1445 606/170 |
| 6,139,508 A | * | 10/2000 | Simpson | A61B 10/06 600/564 |
| 6,334,860 B1 | * | 1/2002 | Dorn | A61B 18/1445 606/48 |
| 2006/0184198 A1 | | 8/2006 | Bales et al. | |
| 2008/0009858 A1 | | 1/2008 | Rizvi | |
| 2009/0012538 A1 | * | 1/2009 | Saliman | A61B 17/0491 606/145 |

FOREIGN PATENT DOCUMENTS

WO 95/08292 A1 3/1995
WO 99/07295 A1 2/1999

OTHER PUBLICATIONS

Dang, Nicholas C. et al. "Surgical Revision After Percutaneous Mitral Valve Repair With a Clip: Initial Multicenter Experience". The Annals of Thoracic Surgery. vol. 1. 80. No. 6. Dec. 1, 2005 (Dec. 1, 2005). pp. 2338-2342.
International Search Report mailed Mar. 11, 2013, issued in corresponding International Application No. PCT/US2012/058139.

* cited by examiner

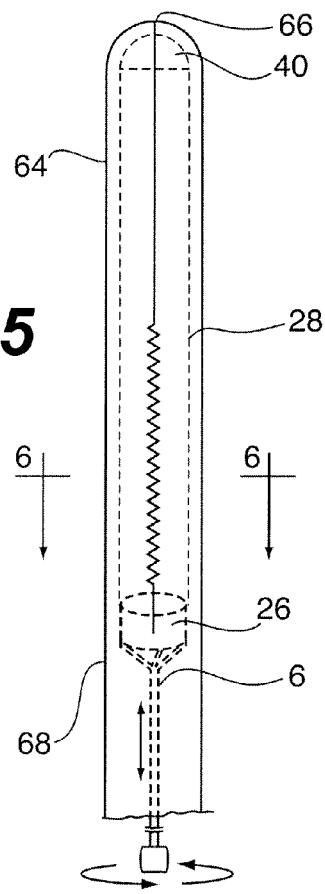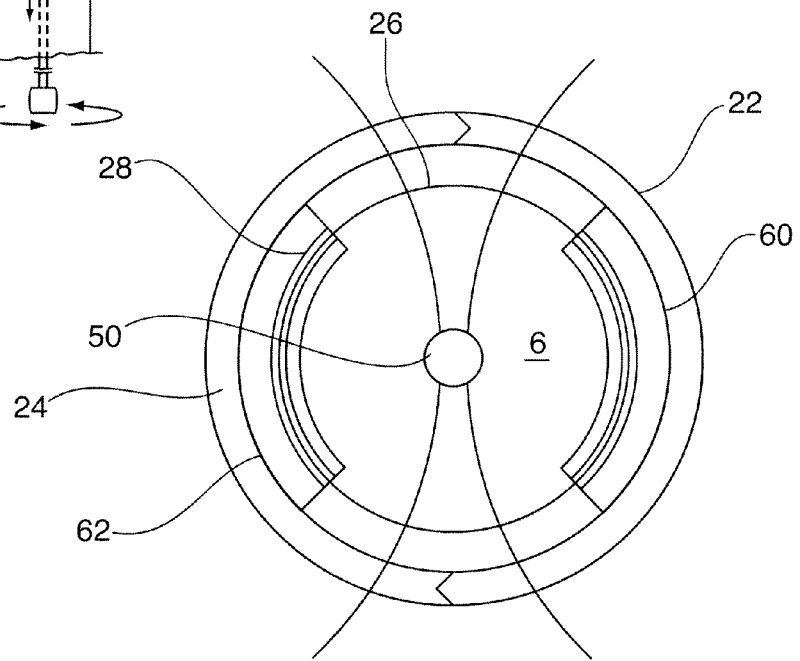

FIG. 8A
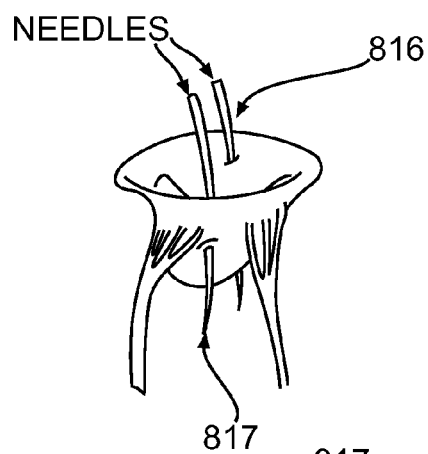
FIG. 8B  FIG. 8C  FIG. 8D
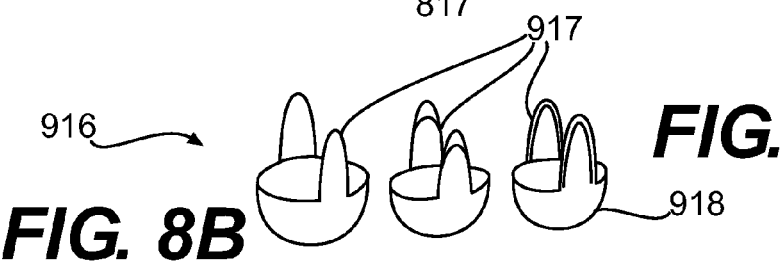
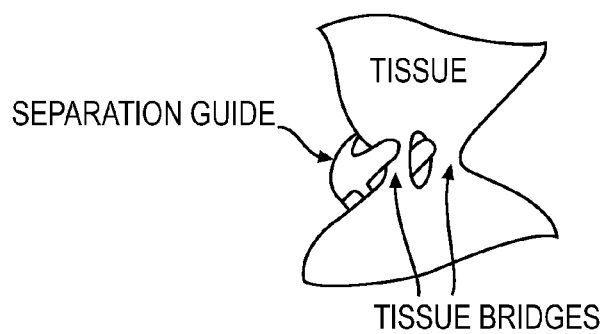
FIG. 8E

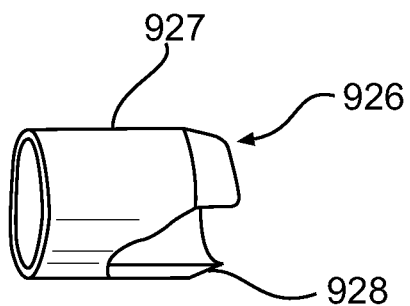
FIG. 9A
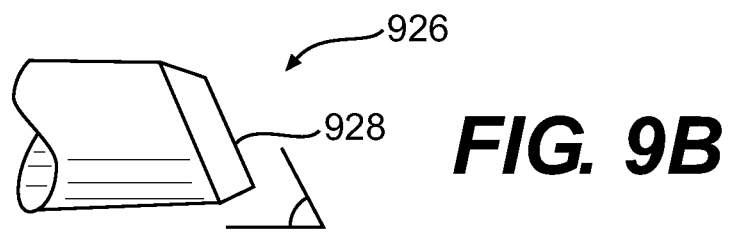
FIG. 9B
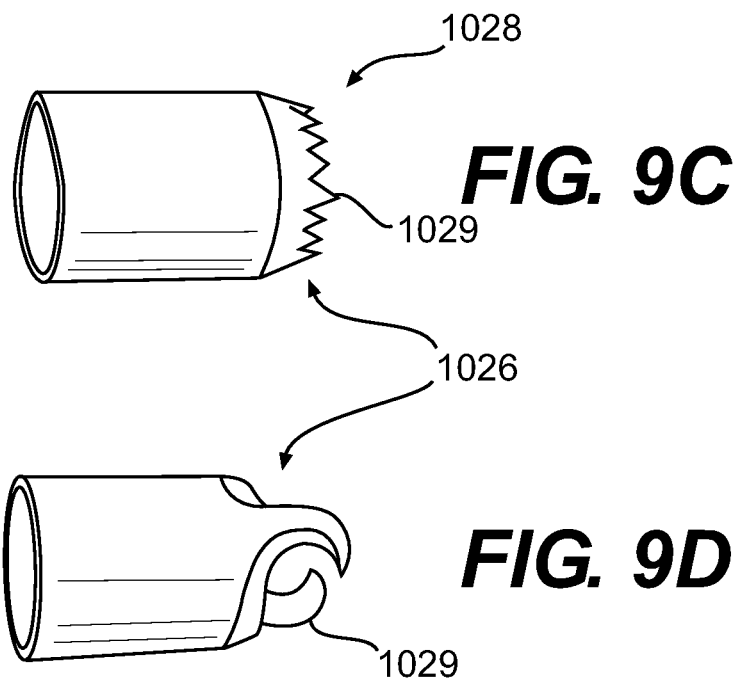
FIG. 9C
FIG. 9D

FIG. 10A  FIG. 10B

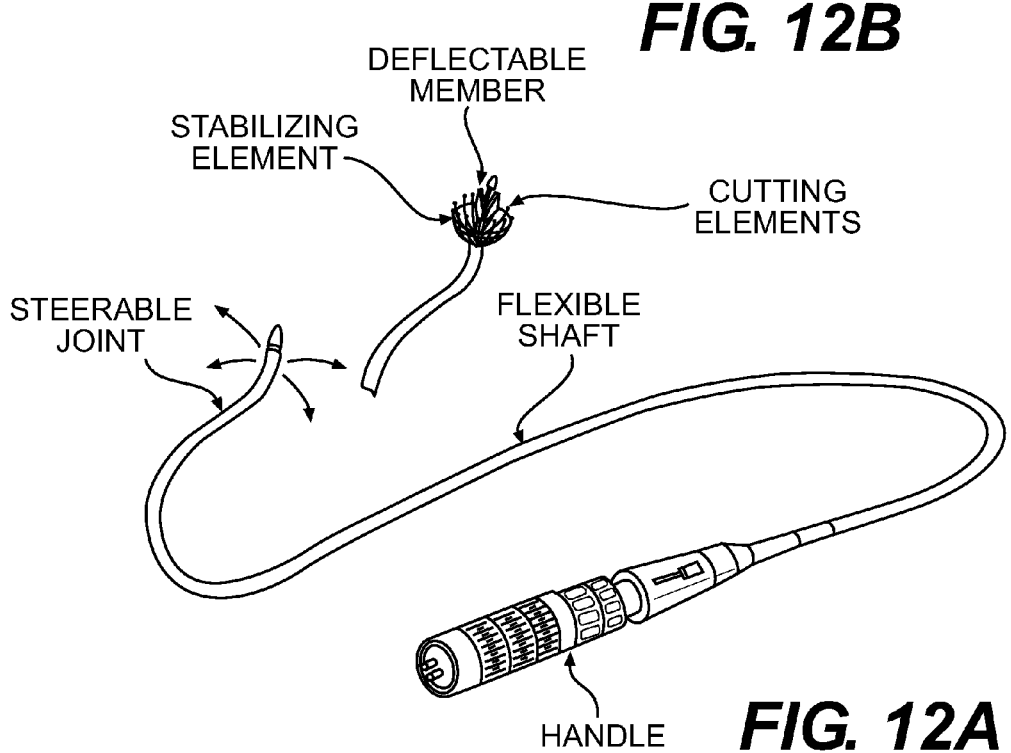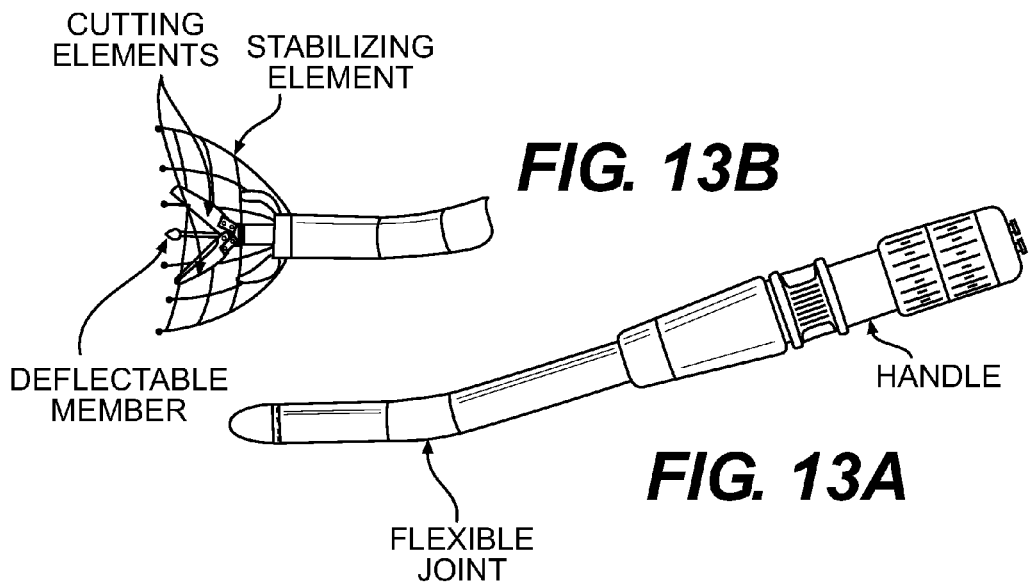

APPARATUSES AND METHODS FOR CUTTING A TISSUE BRIDGE AND/OR REMOVING A HEART VALVE CLIP OR SUTURE

CROSS-REFERENCE TO RELATED APPLICATION

The present application is filed under 35 U.S.C. §371 as a U.S. national phase application of PCT/US2012/058139, having an international filing date of 28 Sep. 2012, which claims the benefit of U.S. provisional patent Application No. 61/540,156, filed Sep. 28, 2011, and U.S. provisional patent Application No. 61/707,856, filed Sep. 28, 2012, the disclosures of which are incorporated herein by reference.

TECHNICAL FIELD

The present disclosure relates generally to medical devices and surgical methods for removing a heart valve clip or a suture and tissue from a heart valve.

BACKGROUND

There are four valves in the heart. These valves are designed to control the flow of blood through the heart to ensure that the blood flows in only one direction. Valves can fail in one of two ways: either they don't open properly, in which case they become stuck (stenotic), or they don't close properly, in which case they become leaky (regurgitant). One valve in particular, the mitral valve, is prone to leaks. A leak in the mitral valve results in a disorder known as mitral regurgitation. Mitral regurgitation occurs when the leaflets of the heart's mitral valve (anterior and posterior) do not close properly thus causing a leak.

During the heart's contraction, a leak in the mitral valve results in a reversal of blood flow. Blood 'backs up' into the left atrium, thereby decreasing blood flow to the body and increasing congestion of the lungs. Although the heart can usually compensate for this leak in the short term, in the long term, the heart loses its ability to compensate, thus leading to gradual or sudden decompensation. Such decompensation includes enlargement of the heart chamber and weakening of the heart muscle. Flooding of the lungs leads to pulmonary edema and pulmonary hypertension, both of which can lead to permanent damage to the lung tissue. Such changes, if detected and corrected early, may be reversible. If left unchecked, such changes will lead to heart failure and death. As such, a severely leaking mitral valve is almost always an indication for surgical repair.

Until recently, the only method for repairing the mitral valve required open heart surgery. Although such an approach has proven benefits, it comes with a certain degree of risk due to the invasiveness of the operation. As such, the risks involved in the operation are often deemed to be too high for some patients, whom, unfortunately, have to be refused treatment. These patients generally go on to die from their disease.

Recently, a new technology was introduced whereby the mitral valve can be repaired through a catheter without the need for surgery. The procedure, known as the MitraClip™ procedure is based on the "Alfieri" method of mitral valve repair whereby a suture is placed surgically to join together the two (anterior and posterior) leaflets of the mitral valve, thus promoting proper closure. As a minimally invasive, non-surgical alternative, the MitraClip™ procedure enables clipping together of the two leaflets, thus creating a bridge, resulting in a double orifice opening. The bridge may include the clip or suture, which eventually heals over with endothelial tissue. The mitral valve continues to open on both sides of the bridge when the heart relaxes, and closes as required when the heart contracts.

The Alfieri and MitraClip® procedures involve, for example, inserting a catheter through a vein in the groin. The catheter is guided up to the mitral valve under x-ray and ultrasound guidance. Once above the valve, the catheter deploys a clip which joins the anterior and posterior leaflets at the midpoint of the valvular opening. The clip effectively reduces the leak, sometimes eliminating it entirely. The procedure is extremely gentle, and very low risk, even in the most elderly and ill patients. This is currently the only device of its kind on the market.

It is expected that the MitraClip™ will remain a first line therapy for treating mitral regurgitation in selected patients for a number of years. However, new technologies are currently under development which would allow the mitral valve to be replaced entirely through a catheter (Transcatheter Mitral Valve Replacement). Although these technologies are still some time away from clinical application, they may provide an alternative to the Alfieri and MitraClip™ procedures in select patients. Furthermore, in cases where the Alfieri or MitraClip™ procedure fails, it is expected that the best option will be mitral valve replacement. Unfortunately, the mitral valve cannot be replaced using transcatheter methods in the presence of a tissue bridge, suture or clip. There is therefore a need for a minimally invasive, catheter based approach to safely remove a tissue bridge, a MitraClip™, a suture, or any other clip device.

There are currently numerous medical devices in use for the removal of tissue from body cavities. However, these devices are not appropriate for use in removing tissue from the heart. Instrumentation for use in heart procedures is very different than instrumentation that may be used in other parts of the body. Firstly, the heart is blood filled, such that no direct visualization can be used, as would be the case with endoscopic devices. Secondly, the heart is mobile and continuously beating, making instrumentation more difficult and potentially hazardous. For these reasons, most cardiac instrumentation involves the use of guidewire technology. This is essential to minimize the risk of cardiac or vascular injury/perforation during manipulation. In contrast, most tissue biopsy devices do not require as exact positioning as do intracardiac devices. Finally, when instrumenting the mitral valve, there is a risk of entanglement of any device with the sub-valvular apparatus which is comprised of a series of cord-like structures which support the valve leaflets, much like a parachute. With guidewire technology, this possibility is mitigated. The ability to steer an apparatus using guidewire technology in the area of the heart valves enables accurate positioning and guidance that is necessary to navigate a clip or suture removing apparatus through two orifices of a double orifice valve.

U.S. Patent Application Publication No. 20080009858A1 discloses a device which is designed to clamp, cauterize, excise and retrieve tissue from the abdomen. This device is not designed to be delivered or applied intravascularly. Moreover, the device could not be utilized intravascularly as electrocautery is ineffective in the presence of a fluid interface. Instead, the device is designed solely for endoscopic use within the abdomen, chest or pelvis. The need for electrocautery as an excision tool is for the purpose of ensuring hemostasis (absence of bleeding following excision). This is not an issue within the heart. Further, the device is not designed to be compatible with guidewire technology.

U.S. Patent Application No. 20060184198A1 discloses a device which is a biopsy forcep designed for use endoscopically. The device consists of jaws which grasp a tissue and a knife which cuts tissue within the jaw. The device is not designed to be used intravascularly and cannot be used with guidewire technology. In addition, the device would not be safe for use within the heart, as the piercing blade is not retractable. In the case of the mitral valve, the blade would be exposed to heart tissues when the jaws are open, thus increasing the risk of injury to normal structures. The cutting mechanism enables for a linear incision within a single plane rather than a circumferential incision, which would be necessary for excision of a mitral tissue bridge.

In some aspects, it may be desirable to provide an apparatus that effectively and safely removes a clip or a suture from the mitral valve to enable placement of a new mitral valve. The device must also be able to safely retrieve the excised clip, suture and/or tissue bridge to prevent intravascular embolization. In some aspects, it may be desirable to provide an apparatus that effectively and safely cuts part of at least one leaflet of the mitral valve to remove the bridge that has been created by the clip or suture. There is a need for such devices that may be deployed through a catheter and which can be used safely and effectively in the heart in proximity to a functioning heart valve.

SUMMARY OF THE INVENTION

The present invention is directed to an apparatus for safely and effectively removing and retrieving a clip, suture, or tissue bridge from a heart valve. The apparatus is operable in association with a guidewire for positioning the device in proximity to a functioning heart valve. The apparatus includes a retractable blade for cutting a tissue bridge which may include a clip or suture, along with a means for removing/retrieving the clip or suture along with the excised tissue from the heart.

In an exemplary embodiment, the apparatus includes a shaft attached to two arm members that secure the clip or suture (along with its tissue bridge) when in a closed position. A retractable blade is located within the shaft and is moveable in the shaft to core out a central portion of a tissue bridge including the clip or suture. A cap is connected to the two arms. The cap is moveable through the arm members in order to enable retrieval of the excised tissue bridge and clip or suture into a chamber within the shaft upon opening of the arms.

According to one aspect of the invention, there is provided an apparatus for excising and removing a clip or suture attached to a heart valve, the clip or suture forming a tissue bridge in said heart valve, the apparatus comprising: an elongate shaft defining a hollow interior, said shaft having a first end and a second end; a handle attached to the second end of the shaft; an elongate clamping member for engaging and securing said clip or suture, said clamping member being attached to the first end of the shaft, the clamping member having a first end attached to the shaft and a second end, the clamping member including two arm members being moveable between an open position where the arm members are spaced apart and a closed position where the arm members are closed in abutting engagement; the arm members being configured to engage said clip or suture in the closed position, each of said arm members defining a longitudinal passageway; a blade located in said interior of said shaft and being moveable longitudinally in said shaft and in said passageways of said arm members when the arm members are in the closed position, between said second end of the shaft and the second end of said clamping member, the blade being configured to completely encompass said clip or suture and tissue bridge for cutting said tissue bridge when the arm members are engaged to said tissue bridge in said closed position; a clamping member actuating member attached to the handle, said clamping member actuating member being coupled to the clamping member for actuating the arm members between the open and closed positions; a blade actuating member attached to the handle, said blade actuating member being coupled to said blade for actuating the blade from said second end of the shaft to said second end of said clamping member for cutting said tissue bridge, wherein the apparatus defines a port for receiving said guidewire, the apparatus being configured to move along said guidewire in a heart of an individual in order to bring said arm members into proximity to said tissue bridge.

In some aspects, the apparatus also comprises a retractable cap attached to at least one of said clamping members, the retractable cap being moveable in said passageways of said arm members when the arm members are in the closed position between the second end of said clamping members and the second end of the shaft for retrieving said clip after cutting of said tissue bridge by said blade; and a cap retracting actuating member located on said handle and coupled to said cap for moving the cap between the second end of said clamping members and the second end of the shaft.

According to another aspect of the invention, there is provided an apparatus for cutting a tissue bridge in a heart valve, the apparatus comprising: two elongate cutting members connected by a rotating joint, the cutting members each having a first end and a second end, each of said cutting members defining an inner cutting surface and being moveable between an open position where the cutting members are spaced apart and a closed position where the cutting members are closed with said cutting surfaces in abutting engagement for cutting said tissue bridge; two gripping members, one of said gripping members being attached to the first end of one of said cutting members for actuating the cutting members between the open and closed positions, wherein the apparatus defines an entry port for a guidewire and an exit port for said guidewire, the apparatus being configured to move along said guidewire in a heart.

According to another aspect of the present invention, there is provided a method for excising and removing a clip or suture attached to a heart valve, the clip or suture forming a tissue bridge in said heart valve, the method comprising the following steps: making an incision in a heart muscle; introducing a guidewire through said incision into a heart and through a double orifice formed in a heart valve by a clip or suture; forming a purse string suture at said incision for opening and closing said incision; providing an apparatus for excising and removing a clip or suture attached to a heart valve, the clip or suture forming a tissue bridge in said heart valve, the apparatus comprising: an elongate shaft defining a hollow interior, said shaft having a first end and a second end; a handle attached to the second end of the shaft; an elongate clamping member for engaging and securing said clip or suture, said clamping member being attached to the first end of the shaft, the clamping member having a first end attached to the shaft and a second end, the clamping member including two arm members being moveable between an open position where the arm members are spaced apart and a closed position where the arm members are closed in abutting engagement; the arm members being configured to engage said clip or suture in the closed position, each of said arm members defining a longitudinal passageway; a blade located in said interior of said shaft and being moveable longitudinally in said shaft and in said passageways of said arm members when the arm members are in the closed position, between said second end of the shaft and the second end of said clamping member, the blade being configured to completely encompass said clip or suture and tissue bridge for cutting said tissue bridge when the arm members are engaged to said tissue bridge in said closed position; a retractable cap attached to at least one of said clamping members, the retractable cap being moveable in said passageways of said arm members when the arm members are in the closed position between the second end of said clamping members and the second end of the shaft for retrieving said clip or suture after cutting of said tissue bridge by said blade; a clamping member actuating member attached to the handle, said clamping member actuating member being coupled to the clamping member for actuating the arm members between the open and closed positions; a blade actuating member attached to the handle, said blade actuating member being coupled to said blade for actuating the blade from said second end of the shaft to said second end of said clamping member for cutting said tissue bridge; and a cap retracting actuating member located on said handle and coupled to said cap for moving the cap between the second end of said clamping members and the second end of the shaft, wherein the apparatus defines two ports for receiving said guidewires (one for each orifice), the apparatus being configured to move along said guidewires in a heart of an individual in order to bring said arm members into proximity to said tissue bridge; attaching said apparatus to said guidewires; opening said incision and moving said apparatus along said guidewires into proximity of said tissue bridge; securing said apparatus to said tissue bridge with said clamping member; cutting said tissue bridge with said blade and removing said tissue bridge including said clip or suture with said cap.

BRIEF DESCRIPTION OF THE DRAWINGS

FIG. 5 is a fragment view showing the arms in the closed position (longitudinal);

FIG. 6 is a sectional view taken along the lined 6-6 of FIG. 5 including the heart valve outline;

FIGS. 8A-8E illustrate exemplary guiding arrangements;

FIGS. 9A-9H illustrate exemplary cutting arrangement;

FIGS. 10A-10L illustrate exemplary containment arrangements;

FIGS. 12A and 12B illustrate an exemplary apparatus according to the present disclosure;

FIGS. 13A and 13B illustrate an exemplary apparatus according to the present disclosure.

DETAILED DESCRIPTION

Reference will now be made in detail to specific embodiments or features of the disclosure, examples of which are illustrated in the accompanying drawings. Generally, corresponding or similar reference numbers will be used, when possible, throughout the drawings to refer to the same or corresponding parts.

Figure 1:
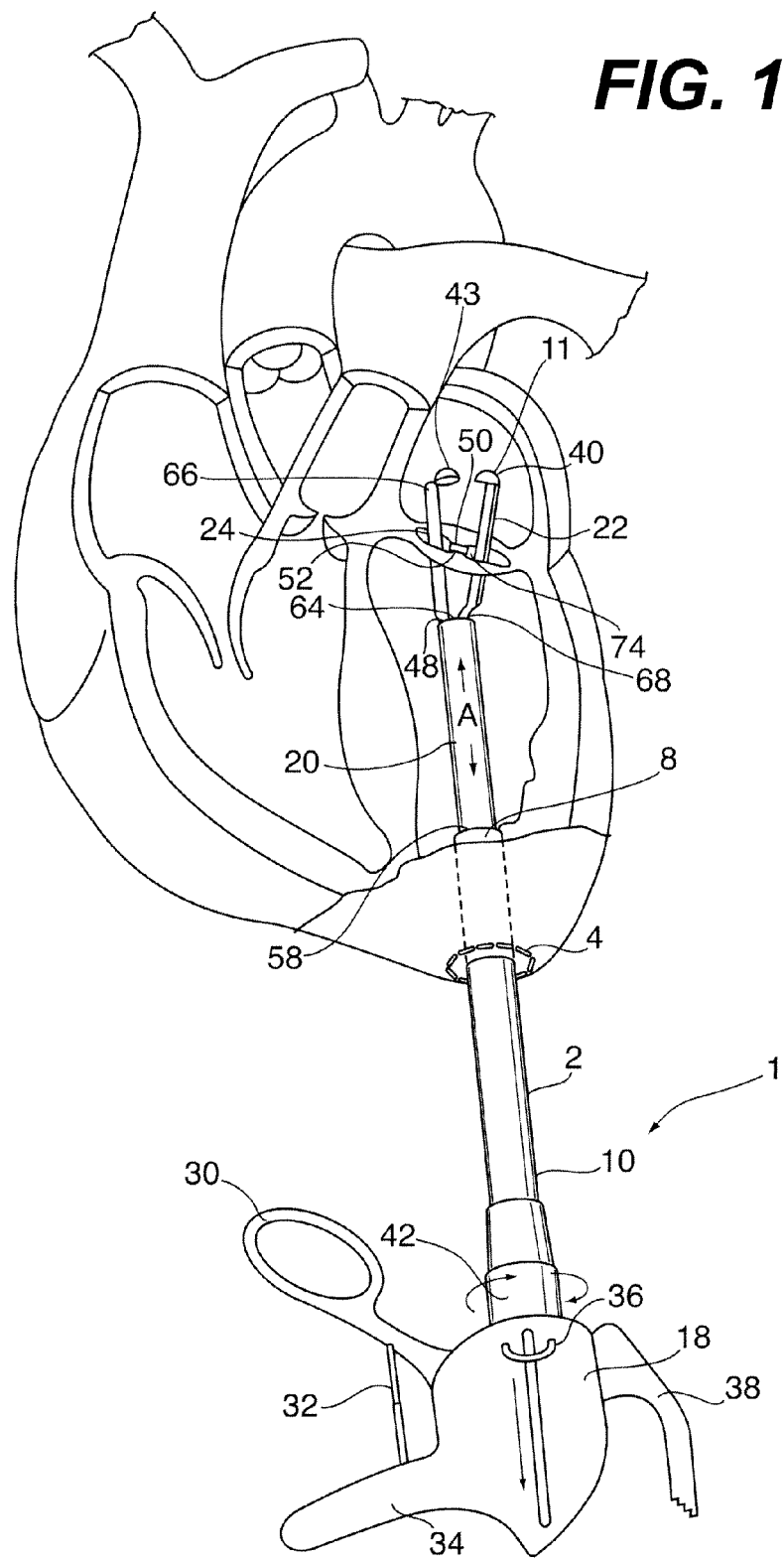
FIG. 1 is a perspective view of an exemplary embodiment of an apparatus according to the present disclosure shown in use in association with a human heart.
Figure 14:
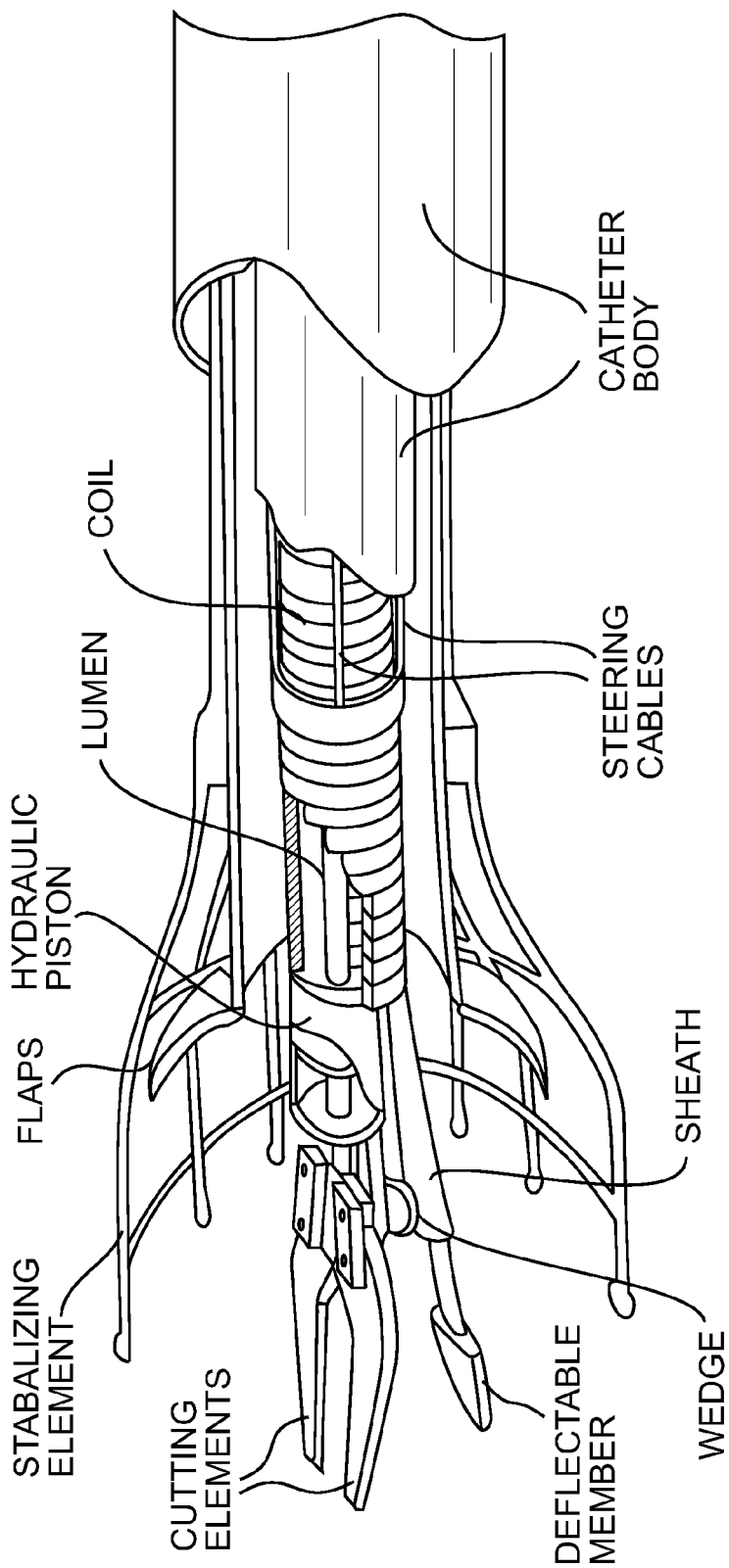
FIG. 14 illustrates an exemplary effective end of the apparatuses of the disclosure.

Referring to FIG. 1, an exemplary apparatus 1 of the present disclosure may be used to remove a tissue bridge 50 including, for example, a clip or a suture that has been secured to the mitral valve of a heart in order to prevent mitral regurgitation. The installation of the clip or suture creates a tissue bridge with a double orifice valvular opening. In some aspects, the clip may be a MitraClip™. Other exemplary apparatuses are illustrated in FIGS. 12-14.

The apparatus 1 comprises an elongate hollow shaft 2. The shaft 2 has a first end 8 and a second end 10. The first end 8 of the shaft 2 defines an opening 58. The shaft is hard and rigid and may be constructed, for example, of stainless steel or a synthetic polymer material such as, for example, Pebax, nylon, polyethylene, poly Polysulfone, Polyimide, polycarbonate, Acrylonitrile Butadiene Styrene (ABS), Poly tetra fluoroethylene (PTFE), Polyethylene Terephtalate (PET), or the like.

Figure 3:
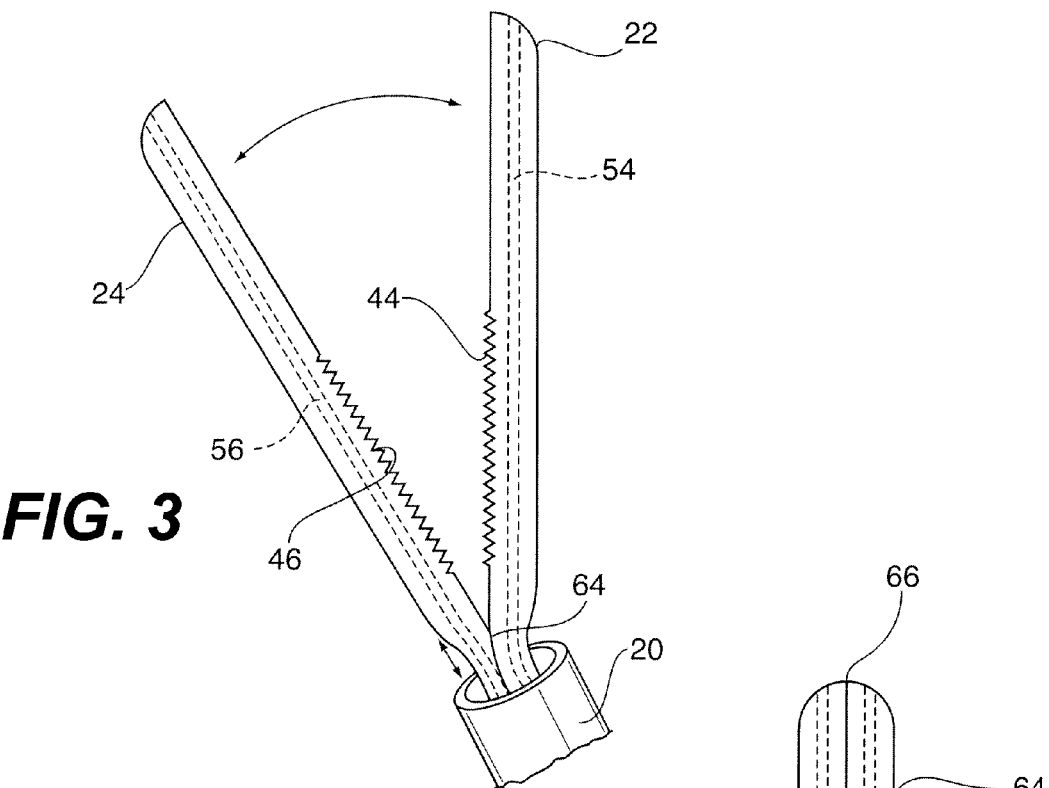
FIG. 3 is a fragment view showing arms of the apparatus in an open position (longitudinal and cross-sectional)
Figure 4:
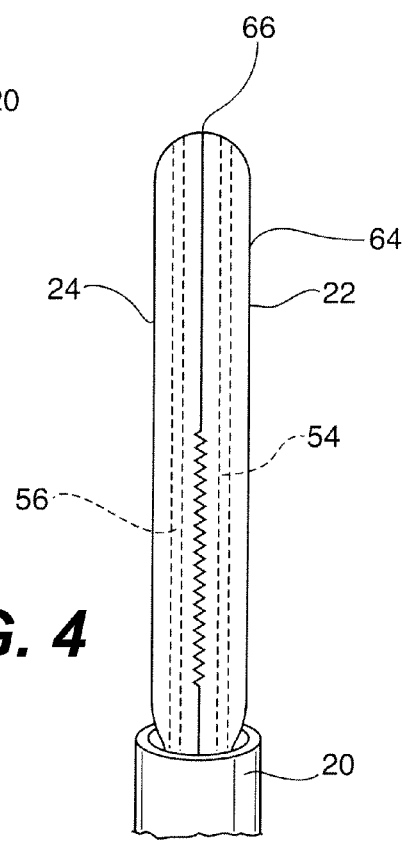
FIG. 4 is a fragment view showing arms of the apparatus in a closed position (longitudinal and cross-sectional)

A distal tube 20 is received in the shaft through the opening 58. The distal tube 20 is disposed in the shaft 2 for telescoping movement therein. The distal tube 20 is hollow and has an open first end 48. A clamping member 64 comprising a first elongate arm member 22 and a second elongate arm member 24 is received in the open first end 48 of the distal tube 20. The clamping member 64 has a first distal end 66 and a second proximal end 68. As shown in FIGS. 3 and 4, the first arm member 22 defines an elongate passageway 54 formed therein. The second arm member 24 defines an elongate passageway 56 formed therein. The arm members 22, 24 are attached at a bottom end to form a clamp structure. The arm members 22, 24 may each have a jagged section 44 and 46 respectively formed on inner surfaces thereof. The arm members are moveable between an open position as shown in FIG. 3 and a closed position as shown in FIG. 4. In some embodiments, the arm members 22, 24 are biased to the open position by a biasing member. The distal tube 20 is sized and configured such that movement of the distal tube 20 upwardly out of opening 58 of the shaft 2 actuates the arm members 22, 24 to the closed position as the clamping member 64 is received in the distal tube 20. A person skilled in the art will appreciate that other means for actuating the arm members between the open and closed positions may be employed.

Further, it should be appreciated that various gripping arrangements are contemplated as alternatives to the arm members 22, 24 and jagged sections 44, 46. During the excision process, the excised tissue to be removed needs to be properly gripped so that both the cut and the retrieval can be performed effectively. The gripping device should provide a steady interface between the gripping device and the targeted piece. The gripping device might need to come in contact with a variety of surfaces, such as soft, thin floppy tissue, structures with soft mesh-like surfaces, hard nodules covered with soft slippery tissue, hard nodules with metallic protrusions, structures that exhibit spring-back effects when a pressure is applied, surface that indents or gets perforated easily, or any combination of the above. The gripping device will need to maintain contact with such a surface while in operation. It should be appreciated that various mechanisms that can provide the above-mentioned gripping function. These mechanisms take on many shapes and use different methods to achieve the same goal.

For example, gripping arrangement may be configured as pliers. The pliers may include jagged gripping surfaces or small sharp spikes that can easily embed into soft tissue or meshed surfaces. The tip of the pliers' jaws can be tipped with different teeth configurations and serrations, as would be understood by persons of ordinary skill in the art. The pliers can also have various shapes that can curl around obstructions. This is applicable for excisions done on heart valves where the pliers needs to reach through the valve to grip onto something on the other side of the valve. For example, in the case of a MitraClip™ excision, it might be desirable to grasp the back side of the clip that is hidden by the tissue bridge. For such applications, the pliers can have horizontal bars or long knobs/teeth that protrude perpendicularly to the jaws of the pliers. These long protrusions can also apply a compressive force that is perpendicular to the primary plane of motion of the pliers, which can help pack the excised tissue into a very compact shape for easy extraction. In some aspects, the pliers can also assume a pointed shape or a cup-like shape with sharpened edge. The pliers can also have more than one pair of jaws, unlike conventional pliers, to ensure uniform gripping from all sides.

Alternatively, the gripping arrangement may comprise an encapsulation mechanism configured to surround as much of the target tissue and clip or suture from all sides. For example, the encapsulation mechanism may include a Chinese finger trap, which is a mesh-like sleeve configured to be slid over the target tissue. The sleeve is then pulled lengthwise to decrease the diameter of the sleeve, thus seizing the enclosed tissue. In some aspects, a fish traps may be used if the desired tissue/implant has a cylindrical protrusion. The fish trap includes a cylindrical cage with an inverted funnel that can be slid over the protrusion. The edge of the inverted funnel may include prongs that point towards the inside of the cage, which prevent the tissue from slipping out once the latter enters the cage. Additional teeth or serrations can line the surfaces and struts of the inverted funnel and the interior of the cage to provide more gripping power.

According to various alternative aspects, the gripping arrangement may comprise articulated scoops with an overall shape like a narrow clamshell, wherein the two halves close around any protrusions that emanate from target tissue/implant. The scoops can assume various shapes. Alternatively, the gripping arrangement may include an inverted sleeve or a coil/spiral configured to cooperate with a threaded cylinder. The gripping arrangement may alternatively comprise suction cups positioned at the tips or sides of end effectors to capture the target tissue/implant; a spiked or barbed cylinder that can retain tissue pushed into the cylinder, for example, via a plunger; or one or more snares configured to capture and retain the target tissue and clip or suture.

As shown in FIGS. 5 and 6, a blade 26 is located in the interior of the shaft 2. The blade 26 may be retractable. In some aspects, the blade 26 is rotatable and moves rotatably. The blade 26 is disposed in the shaft 2 for movement along the length of the shaft 2. The blade 26 is configured to completely encompass the clip and tissue bridge. In some aspects, the blade 26 is circular in shape, but other shapes are within the scope of the present invention.

Figure 9E:
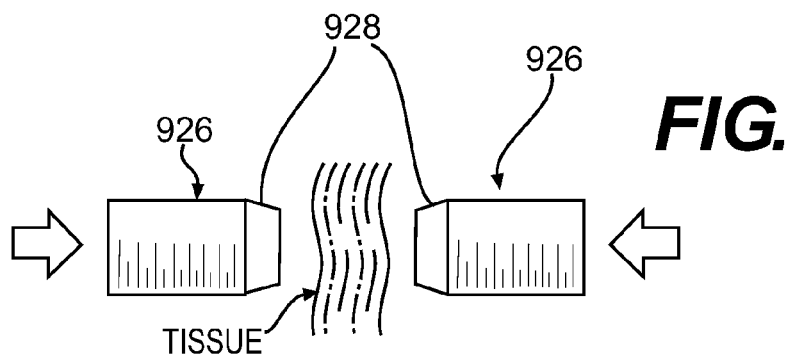

Referring now to FIGS. 9A thru 9H, exemplary embodiments of the blade are illustrated. In some aspects, as shown in FIG. 9A, the blade 926 resembles a biopsy punch. The blade includes a hollow thin-walled metal cylinder 927 in which the edge 928 of one end is sharpened to a razor-like cutting edge.

In some aspects, the only blade movement is a translation along the longitudinal axis of the blade 26 in the direction that moves the cutting edge onto to tissue to be excised. It should be appreciated that the cylindrical blade can have different circumferential shapes including, but not limited to, a circle, an ellipse, a rectangle, a rectangle with rounded corners, etc. The cutting edge 928 can meet the cylindrical wall perpendicularly, or at an angle (FIG. 9B).

According to various aspects, the blade 26 may have two types of movements: the first being a translation along the longitudinal axis of the blade 26 in the direction that moves the cutting edge toward tissue to be excised; and the second being rotation of the cylindrical blade 26 about its longitudinal axis. With this mode of cutting, the cutting edge of the blade imparts on the target tissue both a pushing and a sliding motion. The cylindrical blade in this embodiment will only have a circular circumferential shape.

Referring now to FIG. 9C, a cutting edge 1028 of a cylindrical blade 1026 may be serrated. The serrations 1029 can be uniformly distributed or arranged in a particular manner in which some serrations are of a different size and shape than others. The serrations 1029 can assume the typical triangular shape, or can take other more exotic shapes like that of a sickle (FIG. 9D), spade, or the like.

Figure 9F:
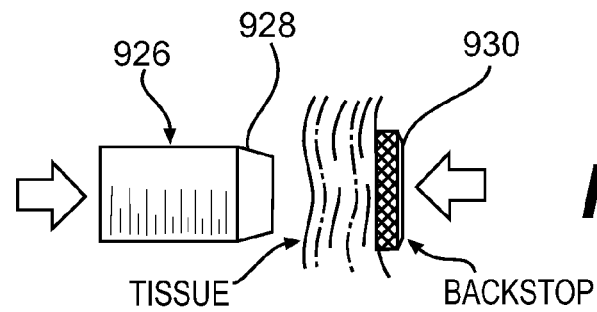
Figure 9H:
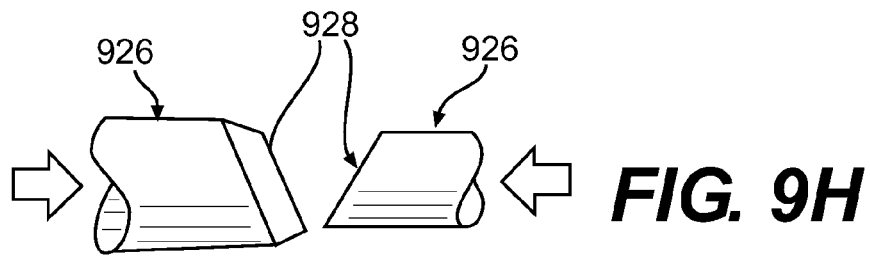
Figure 9G:
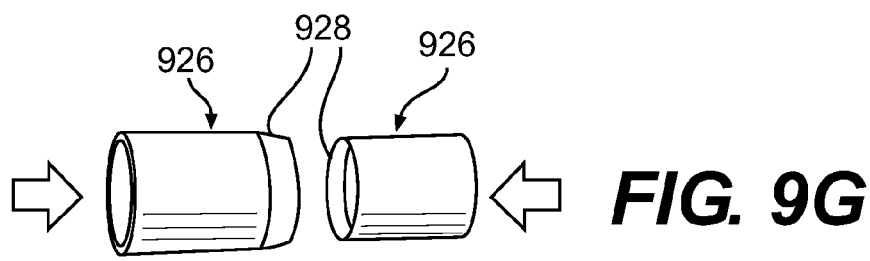

In some aspects, the blade 26 may be the only element of a cutting arrangement, and the one blade is advanced towards the desired tissue throughout the duration of the cutting process. Alternatively, a cutting arrangement 900 may replace the single blade 26. For example, as shown in FIG. 9E, the cutting arrangement 900 may include two blades 926 that can work together acting like jaws, where a target tissue is first positioned between two cylindrical blades 926 having their cutting edges 928 facing each other. Either one or both of the blades 926 can be advanced toward the other until the target tissue is completely cut through. It should be appreciated that the cutting blades 926 can be made such that one is smaller and can be nestled concentrically in the other, as shown in FIGS. 9F and 9G, insuring that the cutting edges 928 can move past each other for a more effective overall cutting motion. According to another aspect, the cutting arrangement may include a blade 926 and a flat backstop 930 that acts as a cutting mat or anvil for the first blade 926 to press against. The target tissue rests on the backstop 930 as the blade 926 is advanced toward the backstop, thus creating a more stable cutting configuration. In any one of the aforementioned embodiments, the blade or blades can also rotate about their longitudinal axes to impart a sliding motion to the cut.

It should be appreciated that a radio-frequency (RF) or an ultrasonic cutting arrangement can be used instead of the mechanical blade. The shape of the RF cutting element or the ultrasonic cutting element can adopt any of the above-described configurations.

Referring again to FIGS. 5 and 6, when the arm members 22, 24 are in the closed position, the hollow shaft, distal tube and passageways 54, 56 define a continuous passageway (not shown) for accommodating movement of the blade 26 from the second end 10 of the shaft 2 to the first end 8 of the shaft 2 and then through the clamping member 64. As shown in FIGS. 5 and 6, a track 28 is may be located in the continuous passageway (not shown) for guiding movement of the blade 26. The track 28 is shown in the clamping member 64 in FIGS. 5 and 6. Blocks 60, 62 may house the tracks.

A cap 40 is attached at the distal end 66 of the clamping member 64. In some aspects, the cap 40 comprises two half sections 11, 43. Half section 11 is attached to the first arm member 22 and half section 43 is attached to the second arm member 24. The cap 40 is configured to be moveable in the continuous passageway (not shown) from the first distal end 66 of the clamping member 64 to the first end 8 of the shaft 2 and then to the second end 10 of the shaft 2.

The second end 10 of the shaft 2 may be attached to a handle 18 that includes actuation means for the various functions of the apparatus 1.

A shaft rotating knob 42 may be attached to the shaft 2 at the second end 10 near the handle 18. The knob 42 is coupled to the shaft 2 and rotates the shaft 2. Rotation of the shaft 2 in turn rotates the arm members 22, 24, which are operatively connected to the shaft, to permit ideal orientation of the arm members 22, 24 during operation of the apparatus 1.

A trigger 30 may be attached to the handle 18. A gripping member 34 may be attached to the handle 18 and is positioned to facilitate pulling the trigger through finger action when an operator of the apparatus grips the handle 18. The trigger 30 is connected to a blade actuating member (not shown) located in the shaft. Many different actuating mechanisms known to a person skilled in the art can be coupled to the trigger 30 for moving the blade 26, upon pulling the trigger 30, from the second end 10 of the shaft 2 through the continuous passageway (not shown) to the distal end 66 of the clamping member. In some embodiments, the blade actuating member is comprised of stainless steel. In some aspects, a safety member 32 is positioned between the trigger 30 and the gripping member 34 to prevent actuation of the blade when the apparatus is not in use. The safety member 32 can be removed when the apparatus is put into use.

A cap retracting handle 36 may be attached to the handle 18. The cap retracting handle 36 is moveable on the handle 18 from a first position to a second actuating position. The cap retracting handle 36 is connected to cap retracting actuating member (not shown) located in the shaft 2. Many different cap retracting actuating mechanisms known to a person skilled in the art can be coupled to the handle 36 for moving cap 40 from the distal end 66 of the clamping member through the continuous passageway (not shown) to the second end 10 of the shaft 2. In an exemplary embodiment, the cap retracting actuating member is comprised of a stainless steel rod.

A lever 38 may be attached to the handle 18. The lever 38 is connected to a clamping member actuating member (not shown) that moves the distal tube 20 upwardly out of the opening 58 at the first end 8 of the shaft 2. The clamping member actuating member is located in the shaft 2. Depression of the lever 38 engages the clamping member actuating member. Many different clamping member actuating mechanisms known to a person skilled in the art can be coupled to the distal tube 20. In some embodiments, the clamping member actuating member is comprised of a stainless steel rod.

Figure 2:
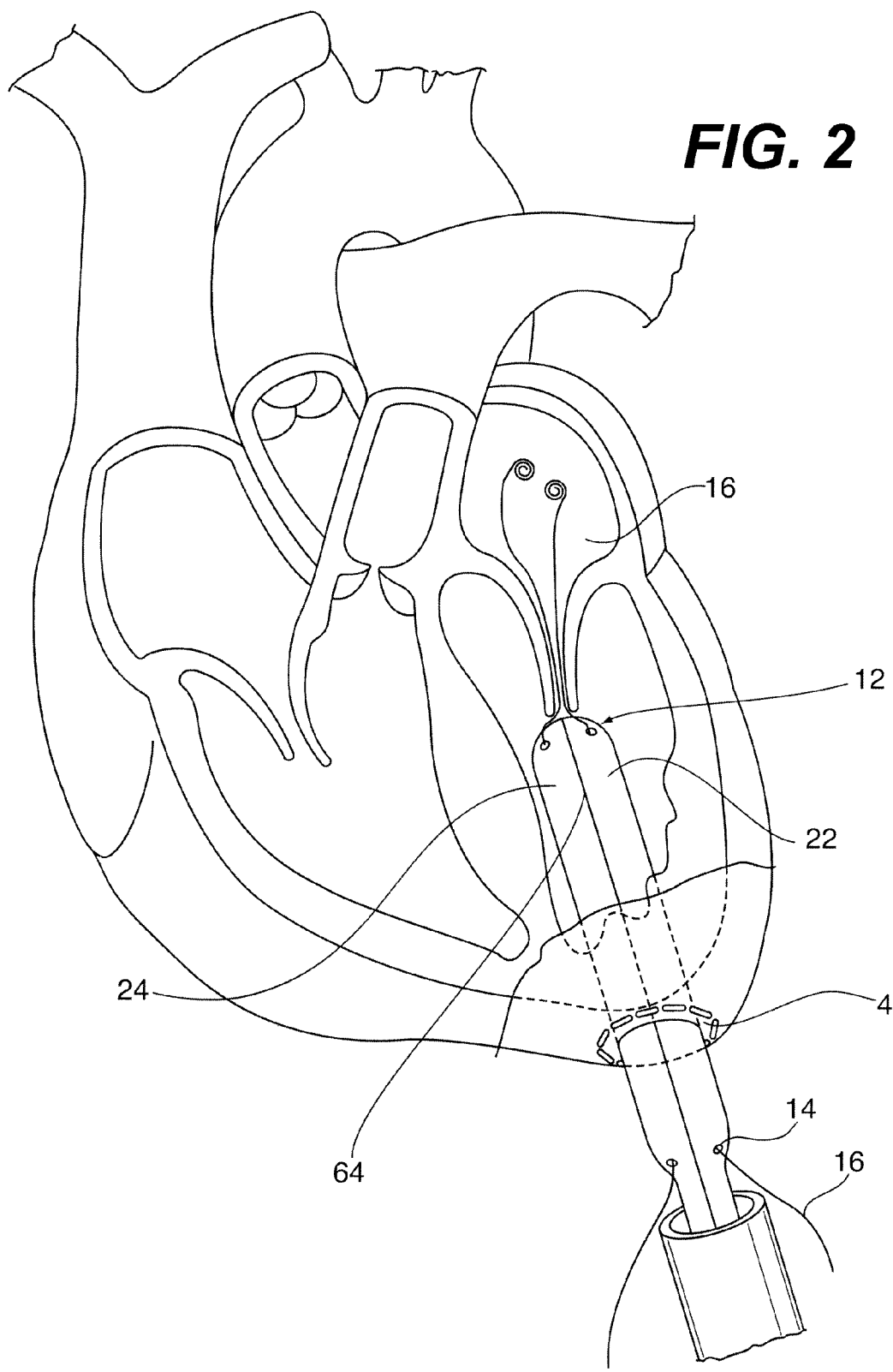
FIG. 2 is a perspective view of the exemplary embodiment showing the apparatus received in the heart.

As shown in FIG. 2, the apparatus 1 defines guidewire entry ports 12 and guidewire exit ports 14 for receiving guidewires 16. The coupling of the apparatus to two guidewires allows for steering of the apparatus in the heart thereby enabling accurate positioning and guidance elements of the apparatus through the two orifices of the double orifice valvular opening. In some aspects, the guidewire entry ports 12 are formed in the distal end 66 of the clamping member and the guidewire exit ports 14 are formed in a proximal end 68 of the clamping member.

Referring now to FIGS. 8A thru 8E, a number of guiding member alternatives to the guidewires 16 are illustrated. FIG. 8A illustrates flexible needles 816, which can be used as guiding members. The needles 816 are long and narrow, similar to guidewires. However, the needles 816 may have sharpened ends 817, which can pierce tissue at target locations, such as mitral valve leaflets. The needles 816 can have different shapes and features, such as barbs and hooks, to facilitate anchoring into the target tissue.

FIGS. 8B-8D illustrate exemplary separation guides 916 that may be used for guiding elements of the apparatus to the target locations. The separation guides 916 may comprise prongs 917 extended from an end effector 918. The separation guides 916 can create larger separations, for example, in the case of multiple tissue bridges, to thereby allow for better device positioning, as illustrated in FIG. 8E. The prongs 917 may include pointed ends (FIG. 8C) or sharpened edges (FIG. 8D), for example, to cut through any tissue or debris that might be obstructing the orifice between two bridges.

Figure 7:
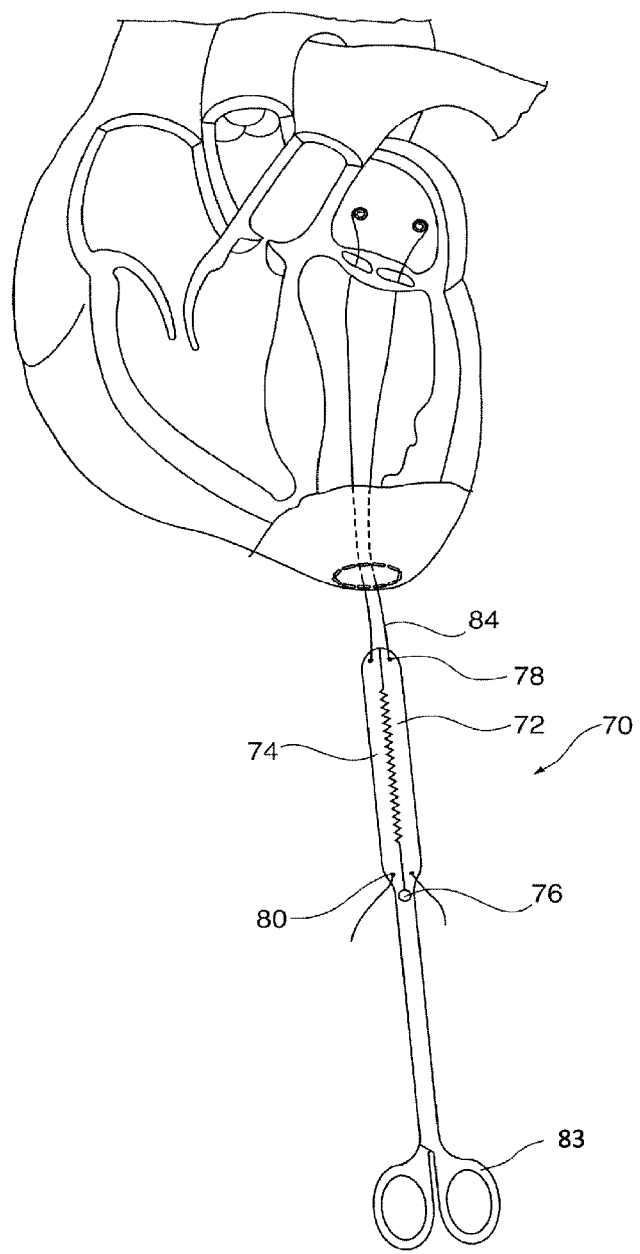
FIG. 7 is a perspective view of an alternate embodiment of an apparatus according to the present disclosure shown in use in association with a human heart.

An alternate embodiment of the present disclosure is shown in FIG. 7. Apparatus 70 is a scissor-like structure comprising two elongate cutting members 72, 74 connected by a rotating joint 76. Each of the cutting members may have a jagged section. The apparatus has a handle 83 for moving the cutting members 72, 74 between an open position and a closed position for cutting tissue. The apparatus 70 defines guidewire entry ports 78 and guidewire exit ports 80 for receiving guidewires 84.

In operation of the exemplary apparatus 1, an incision is made in the heart muscle to create an entry port for the apparatus 1. For example, the entry port may be at the apex of the heart and the apparatus introduced transapically into the left ventricle. Alternatively, the entry port may be transatrial access, which may provide the advantage of direct entry into the left atrium and avoidance of the tendon chordii associated with the left ventricle. A purse string 4 is employed to open and close the incision as required during the procedure. Two guidewires 16 are introduced transapically into the heart through the incision.

The apparatus 1 is then loaded onto the guidewires 16. The guidewires 16 are received through entry ports 12 and then through exit ports 14. Once the apparatus 1 is loaded onto the guidewires 16, the apparatus may then be moved along the guidewires into the heart under x-ray and ultrasound guidance. In some aspects, the apparatus is applied transapically through a small incision in the chest wall.

Alternatively, an apparatus (FIGS. 12A and 12B) can be introduced by an even less invasive percutaneous approach through a catheter without the need for surgery such as introduction via the femoral artery and consequently entering the heart via the aorta and into the right atrium, traversing the septum into the left atrium, and ultimately in a downward direction to access the mitral valve. The procedure involves inserting a catheter through an artery in the groin (femoral artery). In this embodiment, a separate guide catheter (with a piercing dilator) would be used to cross the inter-atrial septum to enable delivery of the device to a position above the mitral valve. This step would be conducted under x-ray and ultrasound guidance.

In order to accommodate the tortuous vasculature through which the apparatus 1 is introduced to access the heart, as well as the controlled articulation required at the distal end of apparatus 1 in order to steer through the inter-atrial septum and through each heart chamber in order to reach the mitral valve, the shaft of apparatus 1 is desirably made of sufficiently flexible material to navigate such complex a delivery route. As with the alternative transapical and transatrial introduction techniques discussed above, during the transfemoral/transeptal introduction technique the distal end of the apparatus is guided to the mitral valve site via a pair of guidewires which have been previously introduced into the double orifice formed by the tissue bridge at the center of the mitral valve. The remainder of the procedure would be performed similarly to the trans-apical approach, albeit with an 'above-valve' approach rather than a 'below-valve' approach.

The cutting device can be introduced either transfemorally or transapically. The transfemoral form of the device (FIGS. 12A and 12B) will incorporate a long shaft that is flexible throughout its length, while the transapical version (FIGS. 13A and 13B) is mostly rigid with the exception of a possible flexible joint.

Particular to the transfemoral form of the device is the inclusion of a steerable joint that the user can control using the handle in order to steer the device and to guide the cutting effective end to its target.

The effective end of both forms of the device, as shown in FIG. 14, see a set of cutting elements, preferably a pair of shearing blades that is attached to the said steerable joint. Superimposed on the cutting elements is a deflectable member that can be used to help move the target tissue towards the cutting elements, or to nudge the cutting elements into the appropriate target region to perform the cut. The entire effective end can be stabilized within the heart using a stabilizing element. The preferred embodiment of such stabilizing element is in form of a flexible retractable cage, made of either metal or polymer.

One possible way to actuate the cutting elements is to use a linkage system that is connected to a hydraulic piston. The piston is connected to the handle using a lumen through which the user can insert/extract an inflation medium (ex: saline) to activate the piston.

The deflectable member is housed in a sheath. The deflectable member is connected all the way to the handle, and the user can push or pull on the said member to extend or retract it out of or into the sheath. Between the sheath and the piston is a wedge that is also connected to the handle. The user can also push and pull the wedge to increase and decrease the space between the sheath and the piston, thus increasing and decreasing the deflection of the deflectable member.

The piston, the piston lumen, and the sheath is bound together by a torsionally stiff metal coil that runs all the way to the handle. The user can push/pull on the coil to extend/retract the entire effective end into or out of the catheter. The user can also impart a twisting motion into the coil to rotate the effective end around the axis of the catheter shaft.

When the effective end is retracted into the body of catheter, the opening is sealed by a set of closing members, preferably flaps, that makes the tip smooth and atraumatic. The catheter body can be made of one or multiple concentric hollow shafts.

Navigation and positioning for both devices is done by both guidewires and through active steering using steering cables. Near the distal end of the coil, a set of steering cables are laid along the entire length of the coil. The cables are place so that they are diametrically opposing each other, and the distal end of the cables is anchored to the distal end of the coil. The proximal ends are connected to the handle. The user can push/pull on these cables to deflect the tip/effective end of the catheter, thus assisting the user in catheter navigation and positioning of the effective end.

The stabilizing element is also connected to the handle, and the user to push/pull on it to deploy it into the heart, or retract it into the catheter.

Figure 11A:
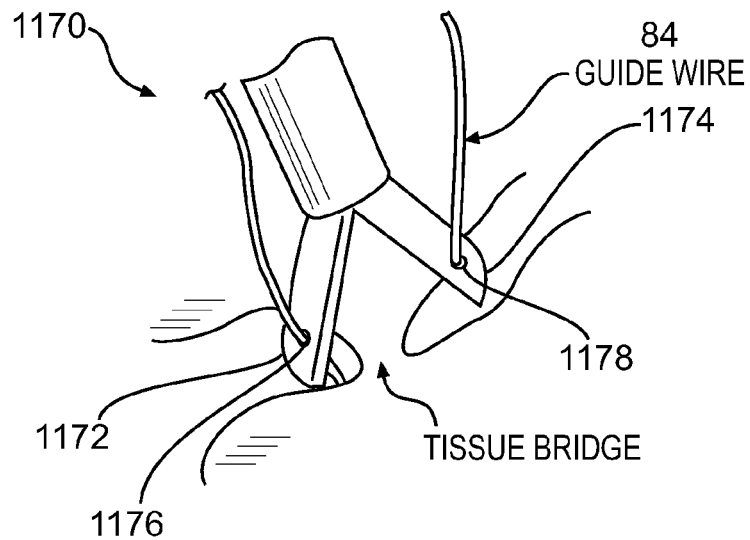
FIGS. 11A and 11B illustrate exemplary cutting arrangements in accordance with the disclosure.

Referring now to FIG. 11A, according to some aspects, a cutting arrangement 1170 may comprise blades 1172, 1174 having holes 1176, 1178 disposed proximate the tips of the blades 1172, 1174. Guidewires 84 can be threaded through the holes 1176, 1178 to help guide the blades 1172, 1174 to the proper position around the tissue bridge. The active cutting mechanism may be one of tissue shearing between the two blades 1172, 1174 sliding past each other. In order to prevent the blades from cutting into any hard inclusions, such as for example a MitraClip®, the blades of the cutting arrangement must be positioned correctly through imaging. Alternatively, the blades 1172, 1174 of the cutting arrangement can be fitted in oversized rounded sheaths (not shown) that extend beyond the cutting edges of the blades 1172, 1174. In such an embodiment, the holes for receiving the guidewires may be disposed in the sheaths. It should be understood that as the scissors are closed around the tissue bridge, the sheaths will push away any hard inclusions that the blades must avoid. Once the sheaths are closed around the tissue bridge, the blades may be released from the sheath to perform the cut.

It should be appreciated that the cutting arrangement may be configured as any desired cutting mechanism. For example, the cutting arrangement may be configured as a single guillotine-shaped blade arranged to cut from one side of the bridge to the other; a single spear-shaped blade with a pointed tip configured to penetrate the center of the tissue bridge and propagates the cut outwardly towards the sides of the bridge; or a sickle-shaped blade configured to be positioned next to the tissue bridge such that the sharpened inner curve of the blade is aligned with the side of the tissue bridge and arranged to cut the bridge by sliding the blade across the bridge, from one side to the other. In some aspects, the blade may be V-shaped with a sharpened inner curve similar to the sickle. Alternatively, the blade can be U-shaped or can even incorporate a set of hinges to allow for folding into a compact package during introduction. The inner curve is arranged to straddle the tissue bridge from the top or the bottom and can then be thrusted through the bridge to perform the cut.

Figure 11B:
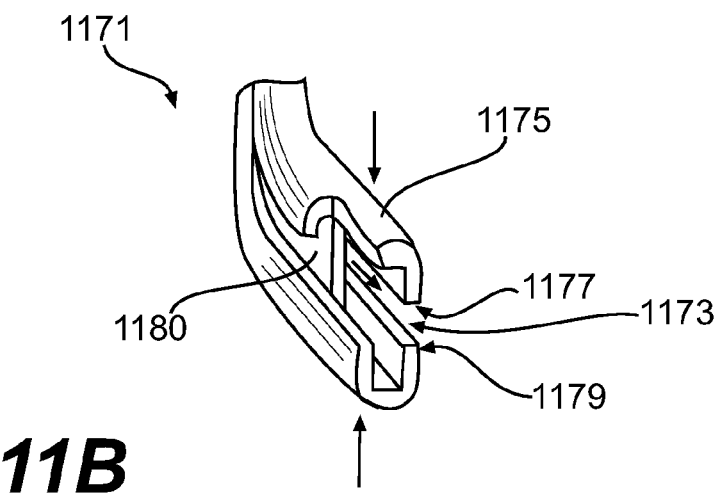

According to some aspects, as shown in FIG. 11B, the cutting arrangement 1171 may include a clamp 1175 configured to secure the tissue bridge from upper and/or lower faces 1177, 1179. The clamp 1175 may include an interior slot 1173 running throughout the entire length of the clamp. When the clamp is engaged onto the tissue bridge, a small blade 1180 housed inside the slot 1173 travels the length of the slot to perform the cut.

It should be appreciated that the cutting arrangement may include circular blade rotatable about a centerpoint, similar to a pizza cutter. A narrow stiff backing plate may be positioned on one side of the tissue bridge, and the circular blade is placed on the opposing side. The plate and the blade are then brought together to sandwich the tissue bridge, and the blade is rolled across the backing plate to perform the cut.

It should be appreciated that a radio-frequency (RF) or an ultrasonic cutting arrangement can be used as the cutting arrangement in any of the aforementioned embodiments. The shape of the RF cutting element or the ultrasonic cutting element can adopt any of the above-described configurations.

The use of guidewire technology is essential to minimize the risk of cardiac or vascular injury/perforation during manipulation. When instrumenting the mitral valve from the transapical (below-valve) approach, there is a risk of entanglement of any device with the sub-valvular apparatus (a series of cord-like structures which support the valve leaflets, much like a parachute). This risk is reduced by use of guidewire technology, and by the steerable nature of the apparatus, which enables accurate positioning and guidance of the arm members through the two orifices of the double orifice valve. The positioning of the guidewires 16 in the heart is shown in FIG. 2.

The arm members 22, 24 can then be applied in the closed position to enable delivery of the apparatus into the cardiac chamber, i.e., the left ventricle. Lever 38 is depressed to a closed position where it is flush with the handle 18. The clamping actuating member is engaged causing the distal tube 20 to advance. This approximates the arm members 22, 24 to the closed position enabling the apparatus to be guided and steered into the heart chamber. Once there is confirmation via x-ray and/or ultrasound guidance that the apparatus 1 is completely within the heart, the lever is lifted thereby disengaging the clamping member actuating member causing the distal tube 20 to retract. This causes the arm members 22, 24 to move to the open position. The arm members are then guided along the previously positioned guidewires through the valve orifices 74 until the arm members 22, 24s straddle the tissue bridge 50.

As shown in FIG. 1, each arm member 22, 24 is in a separate orifice 74 divided by the tissue bridge 50 with the portion of the tissue bridge 50 having the clip or suture between the two arm members 22, 24. The positioning of the arm members 22, 24 may be adjusted by rotating the shaft 2 with the shaft rotating knob 42. In some aspects, the jagged portion 44, 46 of each arm member 22, 24 is positioned to engage the tissue bridge. Once the apparatus is positioned appropriately across the mitral valve, the guidewires can be removed to minimize the risk of guidewire related injury. The lever 38 is then closed to engage the clamping member actuating member thereby moving the distal tube upwardly out of the opening 58 and closing the arm members onto the portion of the tissue bridge 50 containing the clip or suture. The jagged portion 44, 46 of the arm members 22, 24 ensures adequate apposition of the arm members 22, 24 through the tissue when closed.

Once the tissue bridge 50, including the clip or suture, is secured by the arm members 22, 24, and complete inclusion within the closed arms is confirmed (via x-ray guidance), the blade 26 is advanced along the tracks 28 in the shaft 2 upwardly toward the tissue bridge 50. In order to effect this motion, the safety 32 is released and the trigger 30 is pulled thereby actuating the blade actuating member which actuates the blade 26 up the shaft 2 toward the arm members 22, 24. The blade is then actuated through the passageways 54, 56 in the arm members. The blade 26 is configured in a circular manner, such that it has a cutting surface that completely encompasses the clip or suture and tissue bridge 50. As the blade 26 moves upwardly through the passageways in the arm members 22, 24, it cuts the tissue bridge 50 containing the clip or suture, thereby detaching the clip or suture along with its tissue bridge from the mitral valve.

In order to retrieve the tissue that has been cut away and the clip, prior to opening and disengagement of the arms, the cap 40 is retracted from the distal end 66 of the clamping member 64 to the second end of the shaft 10 along the same path as the blade 26. The cap 40 therefore moves the tissue, clip or suture, and blade 26 downwardly along the shaft 2 to the second end 10 of the shaft 2. This action is accomplished by pulling down on the cap retrieving handle thereby actuating the cap retracting actuating member. The tissue and mitral clip or suture are then safely lodged within the base of the apparatus at the second end 10 of the shaft 2. For precautionary purposes, the cap 40 may remain within the base of the apparatus 1 and is not returned to its original position.

At this stage, the actuating lever 38 is lifted thereby disengaging the clamping member actuating member causing the distal tube 20 to retract. This causes the arm members 22, 24 to move to the open position. This maneuver ensures that there is no remaining valvular tissue caught within the arms of the device prior to removal from the heart. While in the open position, the apparatus is retracted such that the arms lie beneath the valve. Once free of the valvular tissue, the arms are carefully closed to facilitate removal of the device from the cardiac chamber. Care is taken to ensure that no cordal structures are caught within the closed arms. The remaining incision is then closed tying down on the previously placed purse-string suture 4.

It should be appreciated that various containment mechanisms are contemplated as alternatives to cap 40. For example, referring again to FIGS. 9E thru 9H, the blade 926 may cooperate with the backstop or a second blade to act as a containment mechanism for excise tissue. In some aspects, the blade may be locked into place relative to the backstop or second blade throughout the remainder of the procedure after excising tissue and the clip or suture.

In an alternate embodiment, as shown in FIGS. 10A and 10B, a multi-segmented cylindrical container can be closed over the entire cutting assembly to enclose the excised tissue. The cylindrical container has one end sealed, then cut into multiple sectors with the cuts all originating from one point of the sealed end and running down the length of the cylinder. These sectors can open up like petals of a flower, and then close up around a target.

Figure 10C:
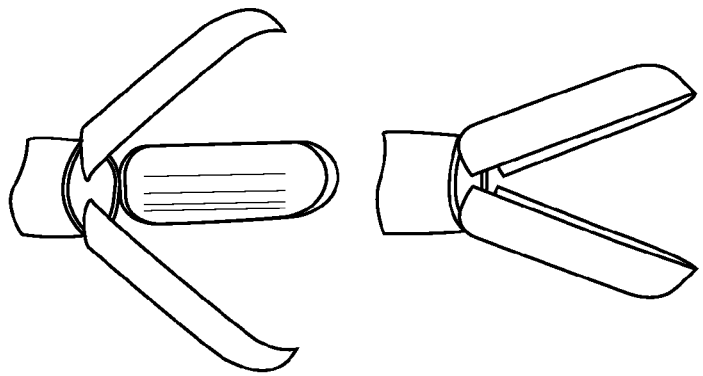
Figure 10D:
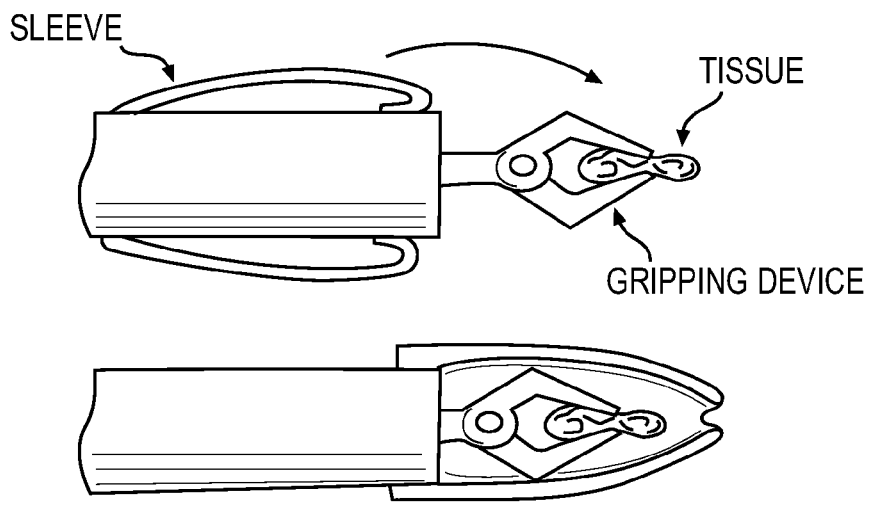

In yet another alternate embodiment, illustrated in FIGS. 10C and 10D, excised target tissue and a clip or suture may be tightly held by the distal end of a gripping device. A flexible, stretchable sleeve can be mounted a priori onto the gripping device such that the entire distal end of the gripping device is entirely covered by the sleeve. The sleeve extends beyond the distal end of the gripping device. The distal end of the sleeve can be shaped such that the distal opening of the sleeve is very small. The proximal end of the sleeve is fixed and/or sealed onto the gripping device. The sleeve can be pulled back and inverted. Once the excised tissue is captured by the gripping device, the sleeve can be folded forward to hide and protect the catch.

Figure 10E:
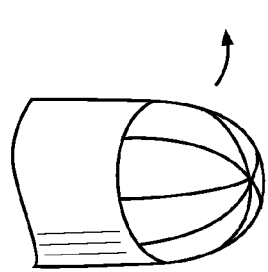
Figure 10F:
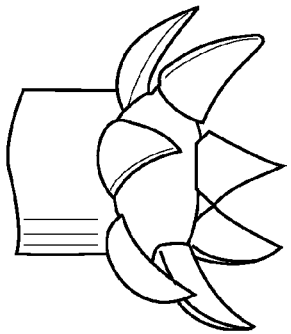

According to another embodiment, as illustrated in FIGS. 10E and 10F, a cylindrical container may include a dome sealing the distal end. The dome is split into slices that originate radially from a point on the dome. The slices meet the cylindrical wall at joints that allow the slices to fold backwards to expose the opening of the cylinder. The slices can be powered or passive. A piece of excised tissue can be retrieved by a gripping device housed inside this container, which is then retracted and sealed into the container.

Figure 10G:
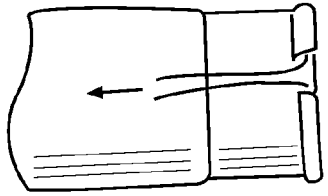
Figure 10H:
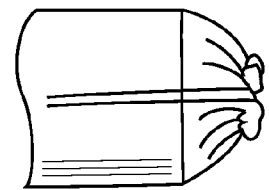

In another embodiment, shown in FIGS. 10G and 10H, a cylindrical container has a soft membrane attached to its distal end, with a drawstring threaded inside. When a gripping device holding the piece of excised tissue is retracted into the cylinder, the drawstring is pulled to seal the cylinder.

Figure 10I:
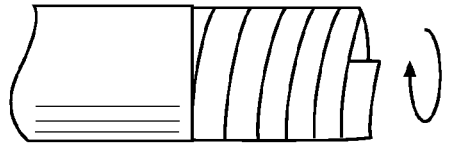
Figure 10J:
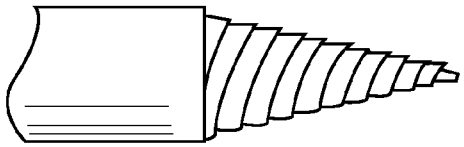

According to yet another embodiment, illustrated in FIGS. 10I and 10J, a cylindrical container has a flexible coil attached at its distal end. The coil is optimally made from a thin but wide ribbon of material, and is shaped in such a way that the coil acts as an extension of the cylinder, conserving both its inner and outer diameters. When a gripping device holding the piece of excised tissue is retracted into the cylinder, the distal end of the coil is induced to twist. This twisting motion will in turn tighten the radius of each of the coil's loops, thus making the coil act like a cap. It should be understood that in some aspects the ribbon may be a shape memory material have the tightened configuration in an unconstrained configuration. The ribbon can be constrained from tightening and then released to the unconstrained configuration upon retraction of the gripping device into the cylinder. It should be appreciated that other known arrangements for expanding and collapsing the ribbon of materials are contemplated by this disclosure.

Figure 10K:
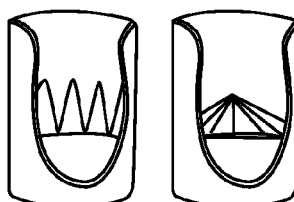
Figure 10L:
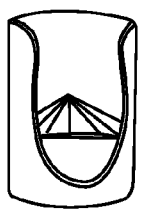

In still another embodiment, as shown in FIGS. 10K and 10L, when a cylindrical container is used, one or more rings of small tabs can be attached to the distal interior of the cylinder. Each tab can be different, however it may be optimal for them to be triangular is shape. Each tab is installed inside the cylinder in such a way that the peak of the triangle is pointing away from the cutting edge. The tabs are in some aspects flexible in nature. When the gripping device is retracted into the distal end of the cylinder while holding onto the excised tissue, the peaks of the tabs can be raised to seal the tube's entrance. The peaks can be raised manually or automatically.

In the alternate embodiment shown in FIG. 7, the apparatus is introduced into the heart in the same manner as with the exemplary embodiments discussed above. This embodiment is designed for use in the chronic scenario i.e. in patients who have had the MitraClip™ in place for months or years, in which case the endothelial tissue has overgrown the implanted clip, and in which case cutting of the tissue bridge would not lead to clip dislodgement/embolization, as the clip would have already been incorporated into the valve leaflet due to tissue overgrowth. In such cases, clip retrieval is not necessary. This design is scissor-like and includes a lengthy and completely flexible snake-like handle, where the scissor tips can be guided by guidewire technology through the two orifices of the heart valve. The cutting members are employed to simply cut out the tissue bridge.

From the foregoing, it will be appreciated that, although specific embodiments have been described herein for purposes of illustration, various modifications or variations may be made without deviating from the spirit or scope of inventive features claimed herein. For example, various elements disclosed herein relative to one embodiment may be usable with one or more additional embodiments, including in some cases interchangeability of the respective parts. Other embodiments will be apparent to those skilled in the art from consideration of the specification and figures and practice of the arrangements disclosed herein. It is intended that the specification and disclosed examples be considered as exemplary only, with a true inventive scope and spirit being indicated by the following claims and their equivalents.

What is claimed is:

1. An apparatus for cutting a tissue bridge in a heart valve, the apparatus comprising:
    two elongate cutting members connected by a rotating joint, the two elongate cutting members each having a first end and a second end, each of the two elongate cutting members defining an inner cutting surface and being moveable between an open position where the two elongate cutting members are spaced apart and a closed position where the two elongate cutting members are closed with the cutting surfaces in abutting engagement for cutting the tissue bridge;
    two gripping members, one of the gripping members being attached to the first end of one of the two elongate cutting members for actuating the cutting members between the open and closed positions; and a respective guidewire within each of the two elongate cutting members,
    wherein the two elongate cutting members each has an entry port for the respective guidewire and an exit port for the respective guidewire, the apparatus being configured to move along each of the respective guidewire positioned within a heart.

2. An apparatus according to claim 1 wherein the gripping members are handles.

3. An apparatus according to claim 1 wherein the inner cutting surfaces define a saw toothed section.

4. An apparatus for cutting a tissue bridge in a heart valve, the apparatus comprising:
    a first elongate cutting member comprising:
        a first member first end and a first member second end;
        a first member inner cutting surface; and
        a first member entry port and a first member exit port through which a first guidewire is within the first elongate cutting member;
    a second elongate cutting member comprising:
        a second member first end and a second member second end;
        a second member inner cutting surface; and
        a second member entry port and a second member exit port through which a second guidewire is within the second elongate cutting member, wherein the first elongate cutting member and the second elongate cutting member are moveable between an open position where the first elongate cutting member and the second elongate cutter member are spaced apart and a closed position where the first elongate cutting member and the second elongate cutter member are closed with the first member inner cutting surface and the second member inner cutting surface in abutting engagement for cutting the tissue bridge and wherein the apparatus is configured to move along each of the first guidewire positioned within a heart and the second guidewire positioned within the heart; and
    a grip being attached to one of the first member first end or the second member first end for actuating the first elongate cutting member and the second elongate cutting member between the open and closed positions.

* * * * *